(12) United States Patent
Alferness et al.

(10) Patent No.: US 7,591,826 B2
(45) Date of Patent: Sep. 22, 2009

(54) DEVICE IMPLANTABLE IN THE CORONARY SINUS TO PROVIDE MITRAL VALVE THERAPY

(75) Inventors: Clifton A. Alferness, Redmond, WA (US); David M. Kaye, Beaumaris (AU)

(73) Assignee: Cardiac Dimensions, Inc., Kirkland, WA (US)

( * ) Notice: Subject to any disclaimer, the term of this patent is extended or adjusted under 35 U.S.C. 154(b) by 2340 days.

(21) Appl. No.: 09/751,271

(22) Filed: Dec. 28, 2000

(65) Prior Publication Data
US 2002/0087173 A1    Jul. 4, 2002

(51) Int. Cl.
*A61B 17/08* (2006.01)
(52) U.S. Cl. .................. 606/151; 606/155; 606/156; 606/157; 623/2.37; 623/2.36; 623/2.38; 623/2.4; 623/2.41
(58) Field of Classification Search .......... 606/151, 606/155, 156, 157; 623/2.37, 372.38, 2.36, 623/2.38, 2.4, 2.41
See application file for complete search history.

(56) References Cited

U.S. PATENT DOCUMENTS

| | | | |
|---|---|---|---|
| 3,995,623 A | 12/1976 | Blake et al. | |
| 4,055,861 A | 11/1977 | Carpentier et al. | |
| 4,164,046 A * | 8/1979 | Cooley | 623/2.36 |
| 4,588,395 A | 5/1986 | Lemelson | |
| 5,061,277 A * | 10/1991 | Carpentier et al. | 623/2.36 |
| 5,350,420 A | 9/1994 | Cosgrove et al. | |
| 5,474,557 A | 12/1995 | Mai | |
| 5,676,671 A | 10/1997 | Inoue | |
| 5,899,882 A | 5/1999 | Waksman et al. | |
| 5,928,258 A | 7/1999 | Khan et al. | |
| 6,096,064 A | 8/2000 | Routh | |
| 6,171,320 B1 | 1/2001 | Monassevitch | |
| 6,210,432 B1 | 4/2001 | Solem et al. | |
| 6,358,195 B1 | 3/2002 | Green et al. | |
| 6,402,781 B1 | 6/2002 | Langberg et al. | |
| 6,419,696 B1 * | 7/2002 | Ortiz et al. | 623/2.37 |
| 6,537,314 B2 | 3/2003 | Langberg et al. | |
| 6,569,198 B1 * | 5/2003 | Wilson et al. | 623/2.37 |
| 6,602,288 B1 * | 8/2003 | Cosgrove et al. | 623/2.36 |
| 6,602,289 B1 * | 8/2003 | Colvin et al. | 623/2.37 |

(Continued)

FOREIGN PATENT DOCUMENTS

EP    0893133    1/1999

(Continued)

OTHER PUBLICATIONS

Papageorgiou, P., et al., "Coronary Sinus Pacing Prevents Induction of Atrial Fibrillation," Circulation 96: 1893-1898, Sep. 16, 1977.

(Continued)

*Primary Examiner*—Nihir Patel
(74) *Attorney, Agent, or Firm*—Shay Glenn LLP

(57) ABSTRACT

A device, system and method provides mitral valve therapy. The device is implantable in the coronary sinus of the heart to partially encircle the mitral valve annulus. The device is elongated, is resilient, and has a preformed arched configuration. When the device is implanted in the coronary sinus, the device exerts a substantially radially inward force to the mitral valve to restore mitral valve annulus geometry.

5 Claims, 3 Drawing Sheets

U.S. PATENT DOCUMENTS

| | | | |
|---|---|---|---|
| 6,626,899 | B2 | 9/2003 | Houser et al. |
| 6,723,038 | B1 | 4/2004 | Schroeder |
| 2001/0018611 | A1 | 8/2001 | Solem et al. |
| 2002/0016628 | A1 | 2/2002 | Langberg et al. |
| 2002/0035361 | A1* | 3/2002 | Houser et al. .................. 606/15 |
| 2002/0049468 | A1 | 4/2002 | Streeter et al. |
| 2002/0065554 | A1 | 5/2002 | Streeter |
| 2002/0103532 | A1 | 8/2002 | Langberg et al. |
| 2002/0138044 | A1 | 9/2002 | Streeter et al. |
| 2002/0169502 | A1* | 11/2002 | Mathis ....................... 623/2.11 |
| 2002/0169504 | A1* | 11/2002 | Alferness et al. ........... 623/2.36 |
| 2003/0018358 | A1* | 1/2003 | Saadat ......................... 606/232 |
| 2003/0069636 | A1 | 4/2003 | Solem et al. |
| 2003/0078465 | A1 | 4/2003 | Pai et al. |
| 2003/0105520 | A1* | 6/2003 | Alferness et al. ........... 623/2.36 |
| 2003/0135267 | A1* | 7/2003 | Solem et al. ................ 623/1.18 |
| 2003/0144697 | A1* | 7/2003 | Mathis et al. ................ 606/232 |
| 2003/0171806 | A1* | 9/2003 | Mathis et al. .............. 623/2.36 |
| 2004/0176840 | A1 | 9/2004 | Langberg |
| 2004/0260342 | A1 | 12/2004 | Vargas et al. |

FOREIGN PATENT DOCUMENTS

| | | |
|---|---|---|
| EP | 1050274 | 11/2000 |
| EP | 1095634 | 5/2001 |
| GB | 0741604 | 12/1995 |
| WO | WO98/56435 | 12/1998 |
| WO | WO 00/60995 | 10/2000 |
| WO | WO 00/74603 A1 | 12/2000 |
| WO | WO 01/00111 A1 | 1/2001 |
| WO | WO01/30248 | 5/2001 |
| WO | WO 01/54618 | 8/2001 |
| WO | WO02/053206 | 7/2002 |
| WO | WO 02/060352 A1 | 8/2002 |

OTHER PUBLICATIONS

European Patent Office Search Reportdated Jul. 28, 2006 for Appln. No. 01991615.4.

Gray, H. Anatomy of the Human Body. The Systemic Veins. Philadelphia: Lea & Febiger, 1918; Bartleby.com. 2000. Available at www.bartleby.com/107/. Accessed Jun. 7, 2006.

Clifton Alferness, et al. U.S. Appl. No. 11/467,105 entitled "Device and method for modifying the shape of a body organ," filed Aug. 24, 2006 (WSGR Reference No. 29912-705.304).

Gregory Nieminen, et al. U.S. Appl. No. 11/458,040, entitled "Mitral Valve Annuloplasty Device with Twisted Anchor," filed Jul. 17, 2006 (WSGR Reference No. 29912-733.501).

Gregory Nieminen, et al. U.S. Appl. No. 11/458,042, entitled "Mitral Valve Annuloplasty Device with Wide Anchor," filed Jul. 17, 2006 (WSGR Reference No. 29912-733.502).

International Search Report for PCT/US01/50860 mailed Oct. 29, 2003.

* cited by examiner

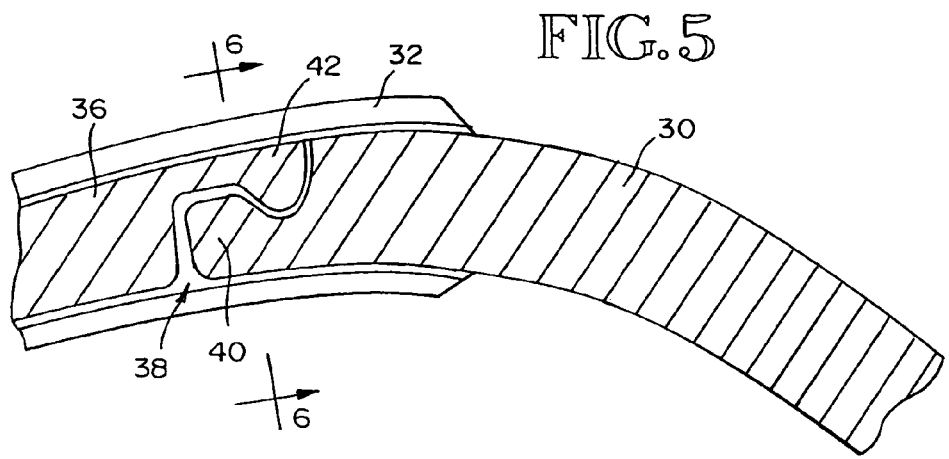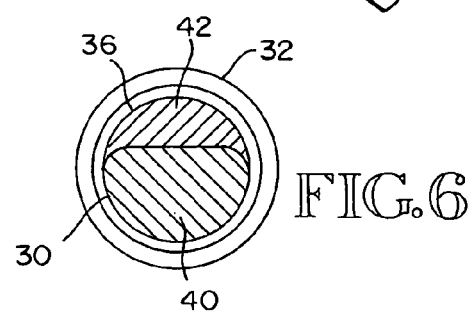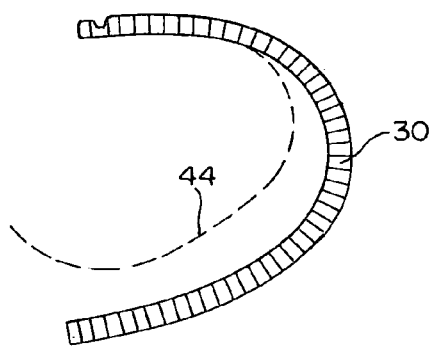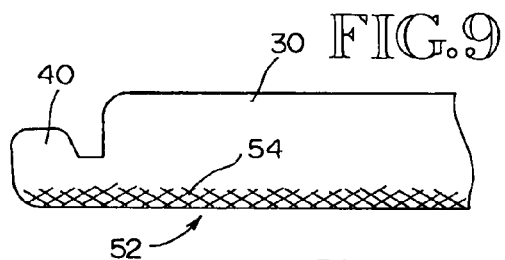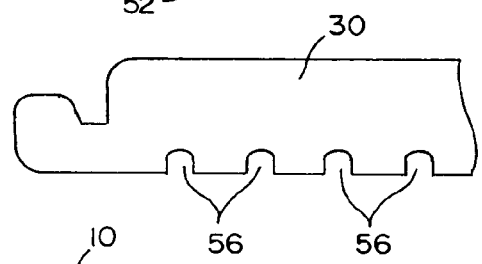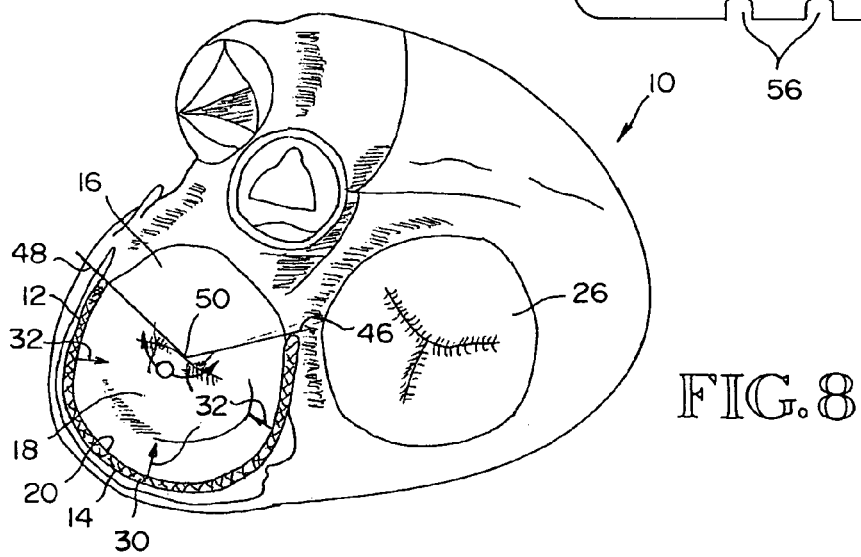

DEVICE IMPLANTABLE IN THE CORONARY SINUS TO PROVIDE MITRAL VALVE THERAPY

FIELD OF THE INVENTION

The present invention generally relates to a device, system and method for treating a deformed heart valve. The present invention more particularly relates to a device, system and method for constricting a mitral valve annulus to correct mitral valve dilation.

BACKGROUND OF THE INVENTION

The human heart generally includes four valves. Of these valves, a most critical one is known as the mitral valve. The mitral valve is located in the left atrial ventricular opening between the left atrium and left ventricle. The mitral valve is intended to prevent regurgitation of blood from the left ventricle into the left atrium when the left ventricle contracts. In preventing blood regurgitation the mitral valve must be able to withstand considerable back pressure as the left ventricle contracts.

The valve cusps of the mitral valve are anchored to muscular wall of the heart by delicate but strong fibrous cords in order to support the cusps during left ventricular contraction. In a healthy mitral valve, the geometry of the mitral valve ensures that the cusps overlie each other to preclude regurgitation of the blood during left ventricular contraction.

The normal functioning of the mitral valve in preventing regurgitation can be impaired by dilated cardiomyopathy caused by disease or certain natural defects. For example, certain diseases may cause dilation of the mitral valve annulus. This can result in deformation of the mitral valve geometry to cause ineffective closure of the mitral valve during left ventricular contraction. Such ineffective closure results in leakage through the mitral valve and regurgitation. Diseases such as bacterial inflammations of the heart or heart failure can cause the aforementioned distortion or dilation of the mitral valve annulus. Needless to say, mitral valve regurgitation must not go uncorrected.

One method of repairing a mitral valve having impaired function is to completely replace the valve. This method has been found to be particularly suitable for replacing a mitral valve when one of the cusps has been severely damaged or deformed. While the replacement of the entire valve eliminates the immediate problem associated with a dilated mitral valve annulus, presently available prosthetic heart valves do not possess the same durability as natural heart valves.

Various other surgical procedures have been developed to correct the deformation of the mitral valve annulus and thus retain the intact natural heart valve function. These surgical techniques involve repairing the shape of the dilated or deformed valve annulus. Such techniques, generally known as annuloplasty, require surgically restricting the valve annulus to minimize dilation. Here, a prosthesis is typically sutured about the base of the valve leaflets to reshape the valve annulus and restrict the movement of the valve annulus during the opening and closing of the mitral valve.

Many different types of prostheses have been developed for use in such surgery. In general, prostheses are annular or partially annular shaped members which fit about the base of the valve annulus. The annular or partially annular shaped members may be formed from a rigid material, such as a metal, or from a flexible material.

While the prior art methods mentioned above have been able to achieve some success in treating mitral regurgitation, they have not been without problems and potential adverse consequences. For example, these procedures require open heart surgery. Such procedures are expensive, are extremely invasive requiring considerable recovery time, and pose the concomitant mortality risks associated with such procedures. Given these factors, such procedures are often reserved as a last resort and hence are employed late in the mitral regurgitation progression. Further, the effectiveness of such procedures is difficult to assess during the procedure and may not be known until a much later time. Hence, the ability to make adjustments to or changes in the prostheses to obtain optimum effectiveness is extremely limited. Later corrections, if made at all, require still another open heart surgery.

SUMMARY OF THE INVENTION

The present invention provides an improved device, system, and method to treat mitral regurgitation. Of particular importance, and in accordance with a salient aspect of the present invention, mitral regurgitation may be treated without resorting to open heart surgery. This is rendered possible by the realization that the coronary sinus of a heart is near to and at least partially encircles the mitral valve annulus. Hence, the device of the present invention may be employed through introduction into the coronary sinus to advantageously effect the geometry of the mitral valve annulus.

The device for effecting the condition of a mitral valve annulus of a heart, in accordance with the broader aspects of the present invention, includes a resilient member having a cross sectional dimension for being received within the coronary sinus of the heart. The device has a longitudinal dimension having an arched configuration for partially encircling the mitral valve and exerting an inward pressure on the mitral valve when placed within the coronary sinus. The inward pressure constricts the mitral valve annulus. This serves to essentially restore the mitral valve geometry to promote effective valve sealing action and to eliminate mitral regurgitation.

The device may be implanted in the coronary sinus using only percutaneous techniques similar to the techniques used to implant cardiac leads such as pacemaker leads. Hence, the present invention also provides a system and method for treating dilated cardiomyopathy which causes mitral regurgitation. The system includes the resilient member and an elongated introducer configured for being releasably coupled to the resilient member. The introducer is preferably flexible to permit it to advance the resilient member into the heart and into the coronary sinus through the coronary sinus ostium. To promote guidance, the system may further include an elongated sheath which straightens the resilient member and which is first advanced into the coronary sinus. Then, the resilient member and introducer are moved through the sheath until the resilient member is in position within the coronary sinus. The sheath may be partially retracted to permit the resilient member to assume its preformed arched configuration. Once the resilient member is properly positioned, the introducer is then decoupled from the resilient member and retracted through the sheath. The procedure is then completed by the retraction of the sheath. As a result, the resilient member is left within the coronary sinus to exert the inward pressure on the mitral valve to restore mitral valve geometry.

In accordance with a particular aspect of the present invention, the resilient member takes the form of a generally C-shaped clip. The clip is resilient to permit straightening during implant. Once implanted in the coronary sinus, the clip is permitted to assume its C-shaped configuration. This enables the clip to exert a substantially radially inward compressive force on the mitral valve annulus.

Since the device, system and method may be employed in a comparatively noninvasive procedure, mitral valve regurgitation may be treated with the device, system and method at an early stage in the mitral regurgitation progression. The device may be placed with relative ease by any noninvasive cardiologist. Since the heart remains completely intact throughout the procedure, the effectiveness of the procedure may be readily determined. Should adjustments be deemed desirable, such adjustments may be made before the patient is sent to recovery.

BRIEF DESCRIPTION OF THE DRAWINGS

The features of the present invention which are believed to be novel are set forth with particularity in the appended claims. The invention, together with further aspects and advantages thereof, may best be understood by making reference to the following description taken in conjunction with the accompanying drawings, and the several figures of which like reference numerals identify identical elements, and wherein:

FIG. 5 is a partial cross sectional view, to an enlarged scale, illustrating a releasable coupling arrangement of the mitral valve therapy device and an introducer in accordance with a preferred embodiment of the present invention;

FIG. 6 is a cross sectional view taken along lines 6-6 of FIG. 5;

FIG. 7 is a plan view illustrating a mitral valve therapy device embodying the present invention shown in a stressed state and an unstressed relative configuration shown in dashed lines;

FIG. 8 is a superior view similar to that of FIGS. 1 and 2 illustrating the relative relation between the mitral valve and an implanted mitral valve therapy device embodying the present invention;

FIG. 9 is a partial plan view, to an enlarged scale, of a fixation arrangement provided on a mitral valve therapy device embodying the present invention; and FIG. 10 is a partial plan view, to an enlarged scale, illustrating an alternative fixation arrangement embodying the present invention.

DETAILED DESCRIPTION OF THE INVENTION

Figure 1:
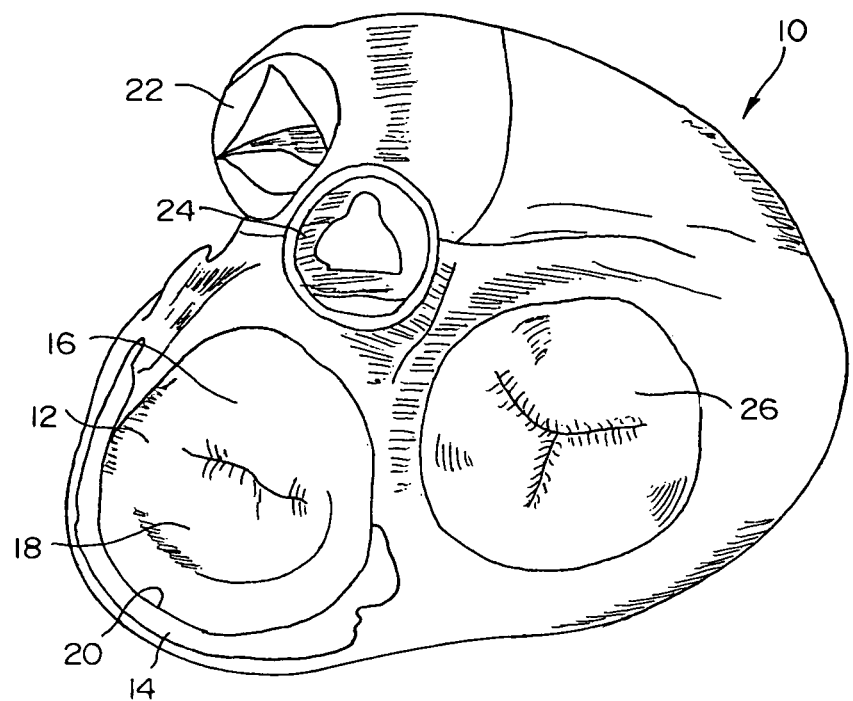
FIG. 1 is a superior view of a human heart with the atria removed.

Referring now to FIG. 1, it is a superior view of a human heart 10 with the atria removed to expose the mitral valve 12 and coronary sinus 14 of the heart 10 to lend a better understanding of the present invention. Also generally shown in FIG. 1 are the pulmonary valve 22, the aortic valve 24, and the tricuspid valve 26 of the heart 10.

More specifically, the mitral valve 12 includes an anterior cusp 16, a posterior cusp 18 and an annulus 20. The annulus encircles the cusps 16 and 18 and maintains their spacing to provide a complete closure during a left ventricular contraction. As is well known, the coronary sinus 14 partially encircles the mitral valve 12 adjacent to the mitral valve annulus 20. As is also known, the coronary sinus is part of the venus system of the heart and extends along the AV groove between the left atrium and the left ventricle. This places the coronary sinus essentially within the same plane as the mitral valve annulus making the coronary sinus available for placement of the mitral valve therapy device of the present invention therein.

Figure 2:
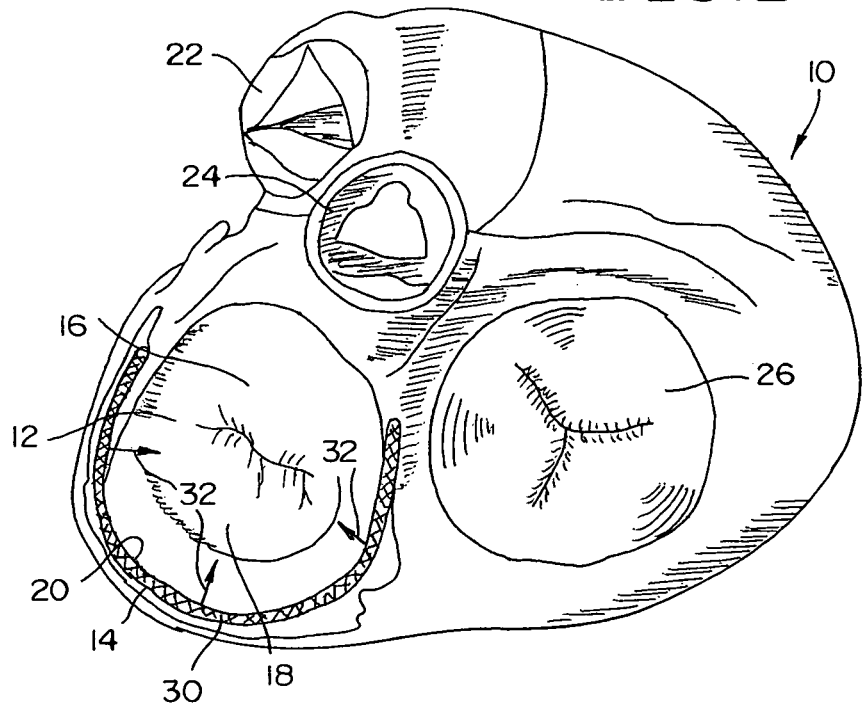
FIG. 2 is another superior view of a human heart with the atria removed and illustrating a mitral valve therapy device embodying the present invention within the coronary sinus and partially extending into the right atrium of the heart.

FIG. 2 shows a mitral valve therapy device 30 embodying the present invention in position within the coronary sinus 14 of the heart 10. As may be noted in FIG. 2, the device is elongated and has an arched configuration. The device also at least partially encircles the mitral valve 12 adjacent to the mitral valve annulus 20. The device 30, by virtue of having an unstressed preformed arched radius smaller than the radius of the dilated mitral valve annulus 20, imparts an inward, generally radial force designated by arrows 32, on the mitral valve annulus 20. This force returns the mitral valve annulus 20 to its original or substantially original geometry to permit the cusps 16 and 18 to more fully come together for sealing the left atrium during left ventricular contraction.

The device 30 has a cross section dimension to be received by the coronary sinus. It is preferably formed of a resilient material to permit the device to be straightened and/or bent for being advanced into the coronary sinus. After being positioned as illustrated, the device is permitted to assume its preformed arched configuration to act upon the mitral valve annulus as previously described. To that end, the device may be formed of, for example, Nitinol, a nickel titanium alloy, well known in the art. This material, as is well known, is capable of being preformed but manipulated to be straight or partially bent while having sufficient memory to return to its preformed configuration. In order to be received within the coronary sinus, the device may have a cross sectional dimension of, for example, on the order of four or five french.

Figure 3:
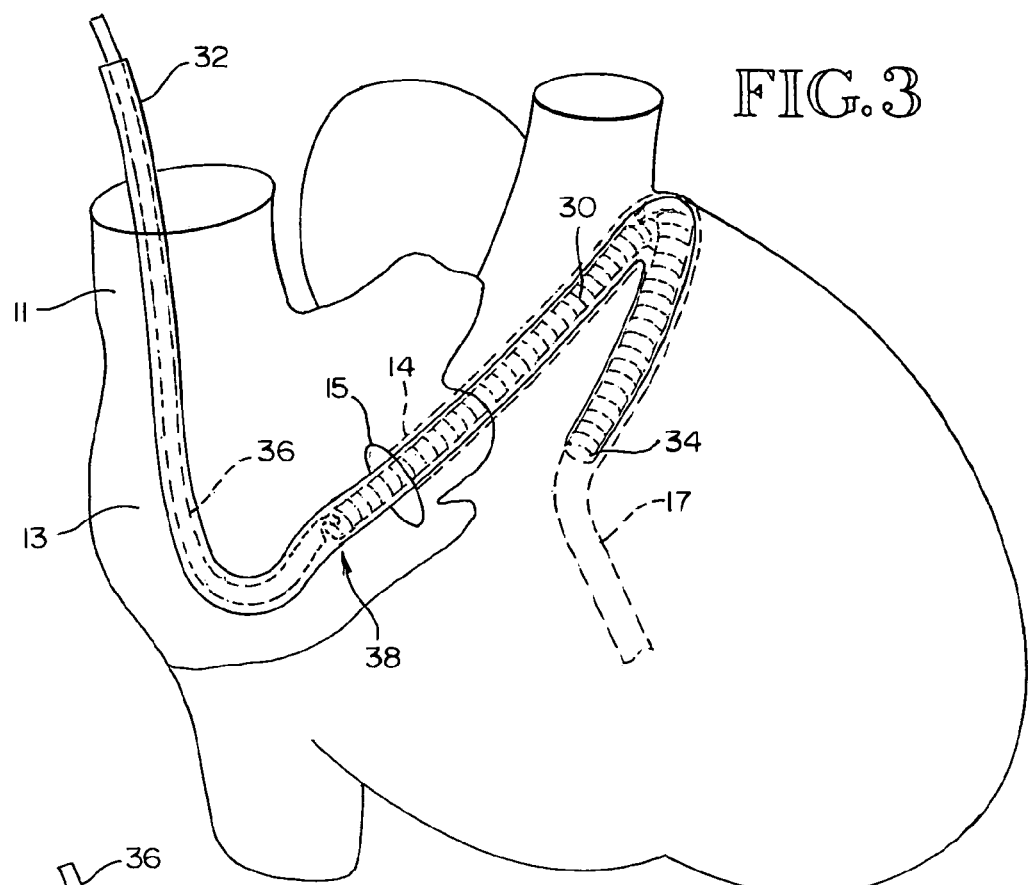
FIG. 3 is a simplified perspective view of a human heart illustrating an intermediate stage in implanting a mitral valve therapy device in accordance with a preferred embodiment of the present invention.

FIGS. 3-6 illustrate a manner in which the mitral valve therapy device may be implanted within the coronary sinus 14 in accordance with a preferred embodiment of the present invention. Referring initially to FIG. 3, an elongated flexible sheath 32 is first introduced into the heart 10 through the superior vena cava 11 into the right atrium 13, and to and through the coronary sinus ostium 15. The sheath 32 is then further advanced into the coronary sinus 14. Advancement of the sheath 32 continues until the distal end 34 of the sheath 32 reaches or slightly enters the great cardiac vein 17. The sheath 32 preferably takes the form of a double-wound polyester catheter. The sheath is dimensioned for receiving the mitral valve therapy device 30 and the introducer 36. To that end, the sheath may have an inner diameter dimension of six french or greater.

The distal end of the introducer 36 and the proximal end of the therapy device 30 each include coupling mechanisms forming a releasable coupling arrangement 38. The coupling arrangement 38 will be described in greater detail subsequently with reference to FIGS. 5 and 6.

The introducer 36 as will be noted in FIG. 3 is elongated and has a diameter dimension similar to the cross sectional dimension of the device 30. The introducer is also flexible. It may be formed of, for example, stainless steel.

Once the sheath 32 is positioned within the heart 10 as illustrated in FIG. 3, the proximal end of the device 30 is coupled to the distal end of the introducer 36. The device 30 and introducer 36 are then fed into the sheath 32. As the device 30 is advanced through the sheath 32 by moving the introducer 36 relative to the sheath 32, the device 30 and introducer 36 follow the path defined by the sheath 32. When the distal end of the device 30 reaches or is near the distal end 34 of the sheath 32, the advancement of the introducer 36 and device 30 is terminated.

The next step is the partial retraction of the sheath 32. This may be best seen in FIG. 4. The sheath 32 is pulled back while the introducer 36 is held stationary. This continues until the distal end 34 of the sheath 32 is proximal to the coupling arrangement of the device 30 and the introducer 36.

Figure 4:
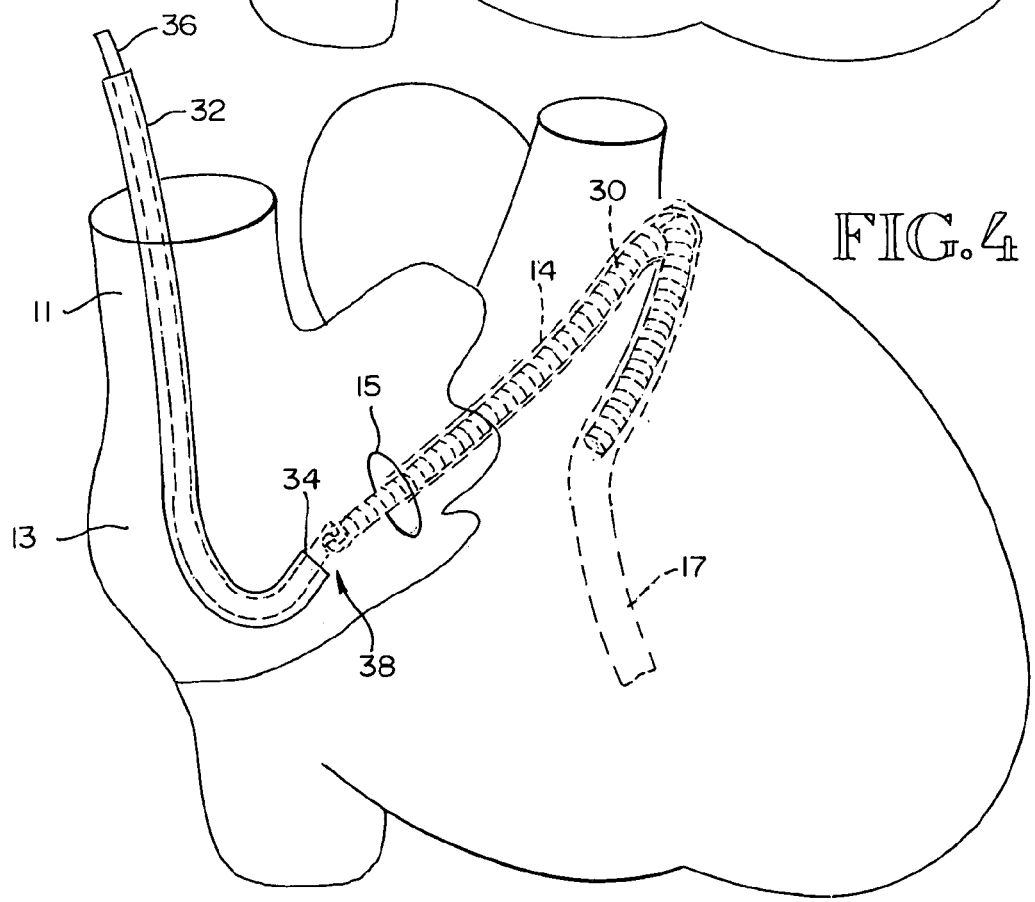
FIG. 4 is a simplified perspective view of a human heart illustrating a further stage in implanting a mitral valve therapy device in accordance with a preferred embodiment of the present invention.

Referring to FIGS. 5 and 6, the coupling arrangement 38 includes a coupling interlock mechanism 40 at the proximal end of the mitral valve therapy device 30 and a complimentary interlock mechanism 42 at the distal end of the introducer 36. After the sheath 32 is retracted where the distal end 34 of the sheath 32 is proximal to the coupling arrangement 38 as seen in FIG. 4, rotation of the sheath and introducer relative to the device 30 releases the introducer 36 from the device 30. The sheath 32 and introducer 36 may now be completely retracted from the patient's heart 10. This leaves the mitral valve therapy device 30 in place within the coronary sinus to act upon the mitral valve annulus to return the mitral valve to a proper sealing function during left ventricular contraction.

FIG. 7 shows the mitral valve therapy device 10 in a stressed condition. The dashed line 44 illustrates the degree of arcuate shifting of the device 30 towards its preformed unstressed state. When first implanted, the device 30 will have a radius of curvature which is greater than its preformed radius of curvature by virtue of the resistance to the device imposed by the heart anatomy. The device, in seeking to migrate to its preformed unstressed state indicated by the dashed line 44, exerts the aforementioned radially inward force on the mitral valve annulus.

FIG. 8 is another view of the heart 10 illustrating the mitral valve therapy device 30 in position within the coronary sinus 14. Here, it may be seen that the device 30 includes a proximal end 46 and a distal end 48. The length of the device 30 is selected so that the included angle theta (θ), defined by the proximal end 46 and distal end 48 together with the center 50 of the mitral valve 12, is preferably greater than 180°. Selecting such a length for the device 30 will assist in the device 30 being held in place and promote a uniform radial force on the mitral valve.

The mitral valve therapy device 30 illustrated in FIGS. 2-8 has sufficient length to project through the coronary sinus ostium into the right atrium so that the proximal end 46 of the device 30 is proximal to the coronary sinus ostium. The device 30 may include additional fixation to hold the device 30 in place. To this end, FIG. 9 shows a fixation element 52 at the proximal end of the mitral valve therapy device 30. The fixation element 52, in accordance with this preferred embodiment, takes the form of a polyester mesh 54 bound to the inner surface of the device 30. This serves to grip heart tissue, such as the right atrial or coronary sinus wall, to maintain the device 30 in its implanted desired position. Alternatively, as shown in FIG. 10, the fixation may be provided by a plurality of teeth 56 formed in the inner surface of the device 30. This alternative arrangement will also provide a gripping action to maintain the device in its proper position.

As can thus be seen from the foregoing, the present invention provides a new an improved device, system and method for treating mitral regurgitation. The device may be employed with only percutaneous techniques. This allows the patient to receive therapy much sooner in the mitral regurgitation progression than previously available with prior art techniques. The cost of the therapy will also be comparatively low making the therapy more generally available. Further, the mitral valve therapy device may be implanted by any noninvasive cardiologist, again lending to the general availability of the therapy. Still further, the device may be readily removed in the event that the therapy is unsuccessful or adjustment is necessary. Lastly, since the heart remains intact and fully functional throughout the procedure, the effectiveness of the therapy may be immediately deduced for optimized adjustment.

While particular embodiments of the present invention have been shown and described, modifications may be made, and it is therefore intended in the appended claims to cover all such changes and modifications which fall within the true spirit and scope of the invention.

What is claimed:

1. A method of treating dilated cardiomyopathy of a heart of a patient, the method including the steps of:
providing a constriction device formed of resilient material having an unstressed C-shape configuration with an effective radius less than a mitral valve annulus and a cross sectional dimension for being received within the coronary sinus of the heart;
advancing the constriction device into the coronary sinus of the heart until the constriction device at least partially encircles the mitral valve of the heart; and
wherein the advancing step includes releasably coupling the constriction device to an elongated flexible introducer and moving the constriction device into the coronary sinus with the introducer.

2. The method of claim 1 including the further steps of releasing the introducer from the constriction device when the constriction device at least partially encircles the mitral valve and removing the introducer from the patient.

3. The method of claim 1 including the further step of placing a cylindrical sheath within the coronary sinus of the heart of the patient, the sheath having a cross sectional dimension for receiving the introducer and constriction device, and wherein the advancing step includes the step of guiding the introducer and constriction device into the coronary sinus within the sheath.

4. The method of claim 3 including the further steps of releasing the introducer from the constriction device when the constriction device at least partially encircles the mitral valve and removing the introducer and sheath from the patient.

5. The method of claim 4 including the further step of retracting the sheath until the sheath is proximal to the constriction device prior to releasing the introducer from the constriction device.

* * * * *

UNITED STATES PATENT AND TRADEMARK OFFICE
CERTIFICATE OF CORRECTION

PATENT NO.      : 7,591,826 B2
APPLICATION NO. : 09/751271
DATED           : September 22, 2009
INVENTOR(S)     : Alferness et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2499 days.

Signed and Sealed this

Twenty-first Day of September, 2010

David J. Kappos
*Director of the United States Patent and Trademark Office*